(12) United States Patent
Grouzmann et al.

(10) Patent No.: US 6,709,651 B2
(45) Date of Patent: Mar. 23, 2004

(54) TREATMENT OF SUBSTANCE P-RELATED DISORDERS

(75) Inventors: Eric Grouzmann, La Conversion (CH); Jean-Silvain Lacroix, Geneva (CH); Michel Monod, Lausanne (CH)

(73) Assignee: B.M.R.A. Corporation B.V., Rotterdam (NL)

( * ) Notice: Subject to any disclaimer, the term of this patent is extended or adjusted under 35 U.S.C. 154(b) by 0 days.

(21) Appl. No.: 09/897,433

(22) Filed: Jul. 3, 2001

(65) Prior Publication Data

US 2003/0007965 A1 Jan. 9, 2003

(51) Int. Cl.$^7$ .............................................. A61K 38/48
(52) U.S. Cl. ................................ 424/94.63; 424/94.64; 424/94.65; 424/94.66; 424/94.67
(58) Field of Search ........................... 424/94.63, 94.64, 424/94.65, 94.66, 94.67

(56) References Cited

U.S. PATENT DOCUMENTS

| | | | |
|---|---|---|---|
| 4,472,305 A | 9/1984 | Hansen et al. | 260/112.5 |
| 4,680,283 A | 7/1987 | Veber et al. | 514/17 |
| 4,839,465 A | 6/1989 | Singh et al. | 530/330 |
| 5,508,433 A | 4/1996 | Achard et al. | 548/515 |
| 5,665,595 A | 9/1997 | Petell et al. | 435/332 |
| 5,795,574 A | 8/1998 | Breton et al. | 424/195.1 |
| 6,063,758 A | 5/2000 | Lappi et al. | 514/2 |
| 6,146,636 A | 11/2000 | Breton et al. | 424/195.1 |
| 6,166,063 A * | 12/2000 | Villhauer | 514/423 |
| 6,251,391 B1 | 6/2001 | Wilkinson et al. | 424/94.63 |
| 6,325,989 B1 * | 12/2001 | Duke-Cohan et al. | 424/9.34 |
| 6,337,069 B1 | 1/2002 | Grouzmann et al. | 424/94.63 |
| 6,395,889 B1 | 5/2002 | Robison | 536/23.2 |
| 6,447,772 B1 | 9/2002 | Houston | 424/94.63 |

FOREIGN PATENT DOCUMENTS

| | | | |
|---|---|---|---|
| EP | 0 394 989 | 10/1990 | C07K/5/00 |
| EP | 0 436 334 | 7/1991 | C07D/207/14 |
| EP | 0 499 313 | 8/1992 | C07D/453/02 |
| EP | 0 514 274 | 11/1992 | C07D/209/44 |
| EP | 0 522 808 | 1/1993 | C07C/217/48 |
| EP | 1 000 930 | 5/2000 | C07C/271/22 |
| WO | WO 97/30990 | 8/1992 | C07D/401/14 |
| WO | WO 93/01165 | 1/1993 | C07C/271/16 |
| WO | WO 93/01169 | 1/1993 | C07D/209/14 |
| WO | WO 93/09116 | 5/1993 | C07D/453/02 |
| WO | WO 99/47152 | 9/1999 | A61K/38/00 |
| WO | WO 02/31134 | 4/2002 | C12N/9/64 |

OTHER PUBLICATIONS

Tanaka et al., Immunopharmacology 40(1): 21–26 (Jul. 1998). Abstract.*
Tanaka et al., International Journal of Immunopharmacology 19(1): 15–24 (1997). Abstract.*
Heins et al., Biochim Biophys Acta 785(1–2): 30–35 (1984). Abstract.*

Abbott, et al., "Cloning Expression and Chromosomal Localization of a Novel Human Dipeptidyl Peptidase (DPP) IV Homolog, DPP8," *Eur. J. Biochem* 267:6140–6150 (2000).
Abbott, et al., "Genomic Organization, Exact Localization, and Tissue Expression of the Human CD26 (Depeptidyl Peptidase IV) Gene," *Immunogemetics* 40:331–338 (1994).
Alving, et al., "Association Between Histamine–Containing Mast Cells and Sensory Nerves in the Skin and Airways of Control and Capsaicin–Treated Pigs," *Cell Tissue Res.* 264:529–538 (1991).
Beauvais, et al., "Dipeptidyl–Peptidase IV Secreted by *Aspergillus Fumigatus*, a Fungus Pathogenic to Humans," *Infection and Immunity* 65:3042–3047 (1997).
Darmoul, et al., "Dipeptidyl Peptidase IV (CD 26) Gene Expression in Enterocyte–Like Colon Cancer Line HT–29 and Caco–2," *J. Bio. Chem.* 267:4824–4833 (1992).
Duke–Cohan, et al., "Attractin (DPPT–L), a Member of the CUB Family of Cell Adhesion and Guidance Proteins, Is Secreted by Activated Human T Lymphocytes and Modulates Immune Cell Interactions," *Proc. Natl. Acad. Sci USA* 95: 11336–11341 (1998).
Grön blad, et al., "Neuropeptides in Synovium of Patients with Rheumatoid Arthritis and Osteoarthritis," *J. Rheumatol.* 15:1807, 1810 (1988).
Hamel, et al., "Tachykinin Involvement in Cutancous Anaphylaxis in the Guinea Pig," *Can. J. Physiol. Pharmacol* 66:1361–1367 (1988).
Heymann, et al., "Liver Dipeptidyl Aminopeptidase IV Hydrolyzes Substance P," *FEBS Letters* 91:360–364 (1978).
Hua, et al., "Pharmacology of Calcitonin Gene Related Peptide Release from Sensory Terminals in the Rat Trachea," *Can. J. Physiol. Pharmacol.* 73:999–1006 (1995).
Kimball, et al., "Substance P. Neurokinin A. and Neurokinin B Induce Generation of II–1–Like Activity in P388D1 Cells," *J. Immunol.* 141 3564–3569 (1988).
Langdon, et al., "Broad Spectrum Neuropeptide Antagonists Inhibit the Growth of Small Cell Lung Cancer in Vivo," *Cancer Res.* 52:4554–4557 (1992).
Levin, et al., "Intraneuronal Substance P Contributes to the Severity of Experimental Arthritis," *Science* 226:547–549 (1984).
Lundblad, "Protective Reflexes and Vascular Effects in the Nasal Mucoa Elicited by Activation of Capsaicin–Sensitive Substance P–Immunoreactive Trigeminal Neurons," *Acta. Physiol. Scand.* 529:1–42 (1984).
Lotz, et al., "Effect of Neuropeptides on Production of Inflammatory Cytokines by Human Monocytes," *Science* 241:1218–1221 (1988).

(List continued on next page.)

Primary Examiner—Jean C. Witz
(74) Attorney, Agent, or Firm—Michael A. Sanzo; Fitch, Even, Tabin & Flannery

(57) ABSTRACT

The present invention is directed to methods of treating a wide variety of diseases, disorders and conditions characterized by excessive activity of substance P. The treatment involves administering peptidases that recognize and selectively cleave polypeptides at Xaa-Pro sequences.

11 Claims, 2 Drawing Sheets

OTHER PUBLICATIONS

Maggi, et al., "Tachykinin Receptors and Tachykinin Receptor Antagonists," *J. Auton. Pharmacol.* 13:23–93 (1993).

Mantyh, et al., "Receptor Binding Sites for Substance P and Substance K in the Canine Gastrontestinal Tract and Their Possible Role in Inflammatory Bowel Disease," *Neuroscience* 25:817–837 (1988).

Mantyh, et al., "Receptor Binding Sites for Substance P. But Not Substance K or Neuromedin K. Are Expressed in High Concentrations by Arterioles, Venules, and Lymph Nodules in Surgical Specimens Obtained from Patients with Ulcerative Colitis and Crohn Disease," *Proc. Natl. Acad. Sci. USA* 85:3235–3239 (1988).

Mentlein, et al., "Proteolytic Processing of Neuropeptide Y and Peptide YY by Dipeptidyl Peptidase IV," *Reg. Peptides* 49:133–144 (1993).

Misumi, et al., "Molecular Cloning and Sequence Analysis of Human Dipeptidyl Peptidase IV, a Serine Proteinase on the Cell Surface," *Biochimica et Biophysica Acta.* 1131:333–336 (1992).

Nagase, et al., "Prediction of the Coding Sequences of Unidentified Human Genes. IX. The Complete Sequences of 100 New cDNA Clones from Brain Which Can Code for Large Proteins in vitro," *DNA Res.* 5:31–39 (1998).

Nakata, et al., "Active Uptake of Substance P Carboxy–Terminal Heptapeptide (5–11) into Rat Brain and Rabbit Spinal Cord Slices," *J. Neurochem.* 37:1529–1534 (1981).

Nieber, et al., "Substance P and β–Endorphin–Like Immunoreactivity in Lavage Fluids of Subjects With and Without Allergic Asthma," *J. Allergy Clin. Immunol.* 90:646–652 (1992).

Otsuka, et al., "Role of Substance P As a Sensory Transmitter in Spinal Cord and Sympathetic Ganglia," *Ciba Foundation Symposium* 91:13–34 (1982).

Otsuka, et al., "Does Substance P Act As a Pain Transmitter?" *TIPS* 8:506–510 (1987).

Sakurada, et al., "Major Metabolites of Substance P Degraded by Spinal Synaptic Membranes Antagonize the Behaviorial Response to Substance P in Rats," *J. Pharm. Sci.* 88:1127–1132 (1999).

Sandberg, et al., "Substance P," *J. Med. Chem.* 25:1009–1015 (1982).

Sannes, "Subcellular Localization of Dipeptidyl Peptidases II and IV in Rat and Rabbit Alveolar Macrophages," *J. Histochem. Cytochem.* 31:684–690 (1983).

Saria, et al., "Release of Multiple Tachykinins from Capsaicin–Sensitive Sensory Nerves in the Lung by Bradykinin, Histamine, Dimethylphenyl Piperazinium, and Vagal Nerve Stimulation," *Am. Rev. Respir. Dis.* 137:1330–1335 (1988).

Stead, et al., "Neuropeptide Regulation of Mucosal Immunity," *Imm. Rev.* 100:333–359 (1987).

Stjärne, et al., "Release of Calcitonin Gene–Related Peptide in the Pig Nasal Mucosa by Antidromic Nerve Stimulation and Capsaicin," *Reg. Peptides* 33:251–262 (1991).

Svensson, et al., "Albumin, Bradykinins, and Eosinophil Cationic Protein on the Nasal Mucosal Surface in Patients with Hay Fever During Natural Allergin Exposure," *J. Allergy Clin. Immunol.* 85:828–833 (1990).

Tattersall, et al., "The Tachykinin NK Receptor Antagonist CP–99,994 Attentuates Cisplatin Induced Emesis in the Ferret," *Eur. J. Pharmacol.* 250:R5–R6 (1993).

Underwood, et al., "Sequence, Purification, and Cloning of an Intracellular Serine Protease, Quiescent Cell Proline Dipeptidase," *J. Bio. Chem.* 274:34053–34058 (1999).

Van Der Belden, et al., "Expression of Aminopeptidase N and Dipeptidyl Peptidase IV in the Healthy and Asthmatic Bronchus," *Clin Experi. Allergy* 28:110–120 (1998).

Vasko, et al., "Prosataglandin E2 Enhances Bradykinin-–Stimulated Release of Neuropeptides from Rat Sensory Neurons in Culture," *J. Neurosci.* 14:4987–4997 (1994).

Yankner, et al., "Neurotrophic and Neurotoxic Effects of Amyloid β Protein: Reversal by Tachykinin Neuropeptides," *Science* 250:279–282 (1990).

Abdel–Ghany, et al., "Truncated Dipeptidyl Peptidase IV Is a Potent Anti–Adhesion and Anti–Metastasis Peptide for Rat Breast Cancer Cells," *Invasion Metastasis* 18:35–43 (1998).

Bou–Gharios, et al., "Expression of Extopeptidases in Scleroderma," *Ann. Rheum. Diseases* 54:111–116 (1995).

Elgün, et al., "Dipeptidyl Peptidase IV and Adenosine Deaminase Activity Decrease in Depression," *Psychoneuroendocrinology* 24 823–832 (1999).

Hildebrandt, et al., "A Guardian Angel: The Involvement of Dipeptidyl Peptidase IV in Psychoneuroendocrine Function, Nutrition and Immune Defence," *Clin. Sci.* 99:93–104 (2000).

Giger, et al., "Study of Enzyme Peptidyl Peptidase IV in Nasal Mucosa," *Schweizerische Medizunsche Wochenschrift Journal Suisse De Medecine* 125:992–1018 (2000).

Kubisova, et al. "Histochemical Study of Depeptidyl Peptidase IV in the Nasal Cavity Organs of Laboratory Rodents and Man," *Sbornik Vedeckych Praci Lekrske Evakulty Karlovy University V Hradei Kralove* 35:285–292 (1992).

* cited by examiner

TREATMENT OF SUBSTANCE P-RELATED DISORDERS

FIELD OF THE INVENTION

The present invention is directed to methods of treating a variety of diseases, disorders and conditions using agents that, effectively, serve as substance P antagonists. The agents are peptidases that selectively cleave at Xaa-Pro amino acid residues.

BACKGROUND OF THE INVENTION

Substance P is a peptide 11 amino acids in length and is a member of the tachykinin family (see U.S. Pat. No. 4,680,283). It is a neurotransmitter that is released by nerve endings in both the central and peripheral nervous systems. Among the numerous biological sites innervated by substance P-releasing neurons are the skin, intestines, stomach, bladder and cardiovascular system (see U.S. Pat. No. 6,146, 636).

Because of its wide distribution, a very large and varied group of disorders have been associated with excessive production of substance P. In particular, substance P has been reported to be involved in the transmission of pain (particularly pain associated with migraine headache), in arthritis, in gastrointestinal disorders, and in emisis (Otsuka, et al., *Ciba Foundation Symp* 91:13–34 (1982); Otsuka, et al., *Tips* 8:506–510 (1987); Sandberg, et al., *J. Med. Chem.* 25:1009 (1982); Levine, et al., *Science* 226:547–549 (1984); Mantyh, et al., *Neurosci.* 25:817–837 (1988); Tattersall, et al., *Eur. J. Pharmacol.* 250:R5–R6 (1993); Gronblad, et al., *J. Rheumatol.* 15:1807–1810 (1988)). Excessive levels of substance P are also believed to contribute to allergic conditions, vasospastic conditions, neurodegenerative disorders and immunological disorders (Hamelet, et al., *Can. J. Pharmacol. Physiol.* 66:1361–1367 (1988); Lotz, et al., *Science* 241:1218–1221 (1988); Kimball, et al., *Immunol.* 141:3464–3569 (1988); Mantyh, et al., *Proc. Nat'l Acid Sci. U.S.A.* 85:3235–3239 (1988); Yankner, et al., *Science* 250:279–282 (1990)).

There have also been reports suggesting that substance P may contribute to certain types of cancer, to autoimmune diseases and to disorders of bladder function (Langdon, et al., *Cancer Res.* 52:4554–4557 (1992); EP 436 334; Luber-Narod, et al, *Lancet* pg. 1239, May 16, 1992). Finally, there are suggestions in the literature that abnormal substance P levels are associated with arthritic diseases, dysthymic disorders, urinary disorders, collagen-related diseases, ophthalmic diseases, drug withdrawal syndromes and certain CNS disorders such as psychoses and schizophrenia (EP 394 989; EP 436,334; Maggi, et al. *J. Auton. Pharmacol.* 13:23–93 (1993)).

Given the extremely broad array of pathologies that substance P has been found to contribute in, it is not surprising that many different substance P antagonists have been developed and tested in the treatment of diseases and conditions. Among the numerous reports that have appeared in the literature discussing such antagonists are the following: U.S. Pat. Nos. 6,146,636; 4,472,305; 4,839,465; EP 499313; EP 522808; WO 93/01165; WO 93/09116; EP 514274; and WO 93/01169. Many of the approaches taken to antagonizing P activity have focused upon agents that bind to and block receptors for this peptide. However, other approaches may be taken to antagonizing substance P activity and these may contribute to the treatment of all of the diseases and conditions described above.

SUMMARY OF THE INVENTION

The present invention is based upon the concept that peptidases that cleave selectively at Xaa-Pro amino acid residues may be administered to patients as a treatment for diseases, disorders and conditions associated with abnormally elevated levels of substance P. The peptidases cleave the first, 2 to 4 residues of substance P thereby producing a peptide, substance P 5-11 that can no longer effectively bind to and activate receptor. Thus, the peptidases act essentially as "antagonists" by reducing the available levels of intact peptide ligand. They may be administered either systemically or locally for the treatment of any of the disorders reported in the literature as being amenable to treatment with substance P antagonists.

In its broadest aspect, the present invention is directed to a method of treating a patient for a substance P-related disease, disorder or condition (collectively "malady") in which a therapeutically effective amount of a peptidase that cleaves selectively at Xaa-Pro sequences is administered. The term "therapeutically effective amount" is a dosage sufficient to produce a significant reduction in one or more symptoms associated with the disease or disorder being treated. For example, in the treatment of conditions such as migraine headache, neuropathic pain, arthritis and inflammatory conditions, a therapeutically effective amount would be a dosage sufficient to reduce the amount of pain or discomfort experienced by the patient. Similarly, a therapeutically effective amount would be a dosage sufficient to reduce the excessive motility associated with conditions such as irritable bowel syndrome or to reduce the rate of tumor growth in small cell carcinoma of the lung. The substance P-related maladies that may be treated are selected from the group consisting of CNS disorders; addiction withdrawal; neuropathic pain; postherpetic pain; neurodegenerative disorders; autoimmune diseases; disorders of the gastrointestinal tract; vasospastic diseases, skin disorders; collagen-related disorders; cardiovascular diseases and conditions; urinary tract disorders; arthritic diseases; ophthalmic diseases; cancer; oedema; emesis; dysthymic disorders; and reflex sympathetic dystrophy.

Preferred maladies amenable to the present treatment method include the following:

a) CNS disorders such as psychosis, anxiety and depression;
b) addiction withdrawal from alcohol or a narcotic;
c) neuropathic pain or postherpetic pain;
d) neurodegenerative maladies such as Alzheimer's disease; AIDS-related dementia, Parkinson's disease, amyotrophic lateral sclerosis, Huntington's disease, and Down's syndrome;
e) autoimmune diseases such as systemic lupus erythmatosus and multiple sclerosis;
f) disorders of the gastrointestinal tract such as colitis, Crohn's disease and irritable bowel syndrome;
g) vasospastic diseases such as migraine headache, Reynaud's disease and angina;
h) disorders or conditions of the skin such as sunburn, psoriasis, dermatitis, uticaria, and inflammation (e.g., due to exposure to poison ivy);
i) collagen-related disorders such as fibrositis, scleroderma, and eosinophilic fascioliasis;
j) hypertension or other cardiovascular diseases and conditions;
k) urinary tract disorders such as incontinence, cystitis, bladder hyper-reflexia, and bladder hypermotility;

l) arthritic diseases such as rheumatoid arthritis and osteoarthritis;

m) ophthalmic diseases or conditions such as proliferative vitreoretinopathy, ocular injury and conjunctivitis;

n) small cell carcinoma of the lung and other cancers; and o) oedema, emesis, dysthymic disorders and reflex sympathetic dystrophy.

As discussed above, the present treatment method involves the administration of a peptidase that cleaves selectively at Xaa-Pro residues. Xaa represents any of the 20 amino acids commonly found in the proteins of animals. The term "selectively cleaves" indicates that the peptidase acts at essentially only these sites in peptides. Preferably, the method utilizes exopeptidases selected from dipeptidyl peptidase IV, quiescent cell proline dipeptidase, dipeptidyl peptidase 8 and attractin. In each case, it is the human form of the peptidase that is preferred. However, peptidases from other species, (e.g., those secreted by *Aspergillus fumigatus*) may also be used provided they have the required specificity. In all cases, it is expected that a therapeutically effective dose for any of the peptidases will be between 1 microgram and 1 milligram. Typically, between 5 micrograms and 500 micrograms will be used.

BRIEF DESCRIPTION OF THE DRAWINGS

FIG. 1 shows changes in percent airway resistance induced by aerosolized histamine (2 mg) in an anesthetized rabbit. Changes were measured before and after the administration of DPP IV (0.1 mg) nebulisation (n=4). Paired t-test, *p<0.05.

FIG. 2 shows the reduction of vascular resistance in the femoral artery of an anesthetized rabbit, induced by histamine, before (darker bar) and after systemic intravenous pretreatment with 26.5 pmol/kg DPP IV (n=5). Paired t test, *p<0.05.

FIG. 3 shows the reduction in vascular resistance in the femoral artery of an anesthetized rabbit, induced by the administration of substance P, before (darker bars) and after systemic intravenous pretreatment with 26.5 pommels/kg DPP IV (n=10). ANOVA, post test: Toukai, *p<0.05, p<0.01; *p<0.001.

DETAILED DESCRIPTION OF THE INVENTION

A. Preparation of Peptidases

Figure 1:
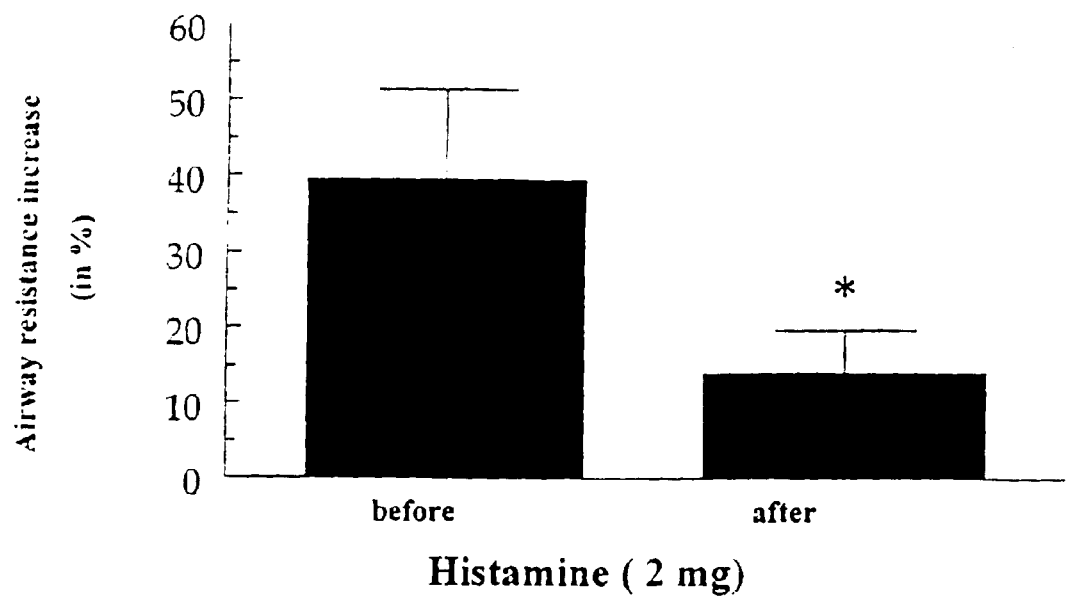
FIG. 1.

The present invention is directed to treatment methods which utilize peptidases that have the common characteristic of cleaving selectively at Xaa-Pro sites. These may be purchased commercially or obtained using any of the procedures described in the relevant literature. For example, the gene corresponding to the peptidase can be isolated and used for recombinant protein production. Especially preferred peptidases, along with references relevant to their isolation and recombinant production, are: human dipeptidyl peptidase IV (Misumi, et al., *Biochim. Biophys. Acta* 15:1131 (1992); Darmoul, et al., *J. Biol. Chem.* 267:4824–4833 (1992); Abbott, et al., *Immunogenetics* 40:331–338 (1994)); human quiescent cell proline dipeptidase (Underwood, et al., *J. Biol. Chem.* 274:34053–34058 (1999)); human attractin (Duke-Cohan, et al., *Proc. Nat'l. Acad. Sci. U.S.A.* 95:11336–11341 (1998); Nagase, et al., *DNA Res.* 5:31–39 (1998)); and human dipeptidyl peptidase 8 (Abbott, et al., *Eur. J. Biochem.* 267:6140–6150 (2000)). In addition to being made recombinantly, these proteins can be synthesized using methods that are well-known in the art.

B. Making of Pharmaceutical Compositions

The peptidases of the present treatment methods may be incorporated into pharmacologically active compositions made in accordance with methods that are standard in the art (see e.g., *Remington's Pharmaceutical Sciences*, 16$^{th}$ ed., A. Oslo Editor, Easton Pa. (1980)). Peptidases will typically be prepared in admixture with conventional excipients. Suitable carriers include, but are not limited to: water; salt solutions; alcohols; gum arabic; vegetable oils; benzyl alcohols; polyethylene glycols; gelatin; carbohydrates such as lactose, amylose or starch; magnesium stearate; talc; silicic acid; viscous paraffin; perfume oil; fatty acid esters; hydroxymethylcellulose; polyvinyl pyrrolidone, etc. The pharmaceutical preparations can be sterilized and, if desired, mixed with auxiliary agents such as: lubricants; preservatives; stabilizers; wetting agents; emulsifiers; salts for influencing osmotic pressure; buffers; coloring agents; flavoring agents; and/or aromatic substances.

Generally, the compositions of this invention will be dispensed in a unit dosage form comprising one or more active compounds in a pharmaceutically acceptable carrier. Dosages for a given patient can be determined using methods well known in the art and will be used to determine the amount of active compound in each unit dosage form. In the case of liquid dosage formulations, it is expected that peptidase will be present in an amount of between 1 µg/ml and 10 mg/ml and, more commonly, at a concentration of between 10 µg/ml and 1 mg/ml. Non-liquid dosage forms will typically contain peptidase in a similar range per unit dose.

C. Dosage Forms and Routes of Administration

The present invention is compatible with any route of administration and any dosage form. Nevertheless, in order to avoid potential degradation of peptides in the gut of patients, parenteral delivery will generally be preferred. Apart from parenteral delivery, agents may be administered orally, topically, perorally, internally, intranasally, rectally, vaginally, lingually and transdermally. Specific dosage forms include tablets, pills, capsules, powders, aerosols, suppositories, skin patches, parenterals, sustained release preparations, and oral liquids including suspensions, solutions and emulsions. If desired, compositions may be freeze-dried and the lyophilizates used for the preparation of products for injection.

All dosage forms may be prepared using methods that are standard in the art (see e.g., *Remington's Pharmaceutical Sciences*, 16$^{th}$ ed., A. Oslo Editor, Easton Pa. (1980)). Solutions can be prepared using water or physiologically compatible organic solvents such as ethanol, 1,2-propylene glycol, polyglycols, dimethyl sulfoxides, fatty alcohols, triglycerides, partial esters of glycerine and the like. Parenteral compositions may be used for intravenous, intraarterial, intramuscular, intraperitoneal, intracutaneous or subcutaneous delivery. The preparations can be made using conventional techniques and may include sterile isotonic saline, water, 1, 3-butanediol, ethanol, 1,2-propylene glycol, polyglycols mixed with water, Ringer's solution, etc.

D. Treatment Methods

Although the present invention includes the treatment of a wide variety of different diseases, the therapeutic objective will always be the same. Specifically, sufficient peptidase must be delivered to a patient to reduce levels of substance P to a point where one or more symptoms associated with the disease being treated are alleviated. For example, a patient being treated for rheumatoid arthritis should receive sufficient drug to alleviate pain associated with this condition.

Similarly, a patient being treated for a neurodegenerative disease or autoimmune disease should receive sufficient peptidase to slow the progression of the disease or reduce one or more of its physical manifestations. The effectiveness of a particular dosage will typically be assessed by clinical examination of patients using methods well known in the art of medicine.

In general, a patient may receive a relatively small dose of peptidase and then administration may be repeated as necessary. For example, a patient may begin by receiving 0.1 mg per day and then increase the dosage upward using changes in symptoms as a guide. It is expected that patients will receive peptidases in unit dosage forms containing between 1 µg and 1 mg, and typically, between 5 µg and 500 µg. Daily dosages may vary between 10 µg and 50 mg and may be provided in either a single or multiple regimen with the latter being generally preferred. In addition, the patient may concurrently receive other agents supplied in the same dosage form or separately. These are simply guidelines, since the actual dose will be determined by the patient and physician based upon a variety of clinical factors.

EXAMPLES

In one set of experiments, the effect of the administration of DPP IV on bronchoconstriction evoked by histamine was studied. Changes in airway resistance in an anesthetised rabbit, either before or after the intratracheal administration of DPP IV, are shown in FIG. 1. The results indicate that significantly less resistance occured after DPP IV treatment. Since histamine acts by inducing the release of neurogeneic substances, including substance P, the results are consistant with the hypothesis that DPP IV inactivates substance P.

Figure 2:
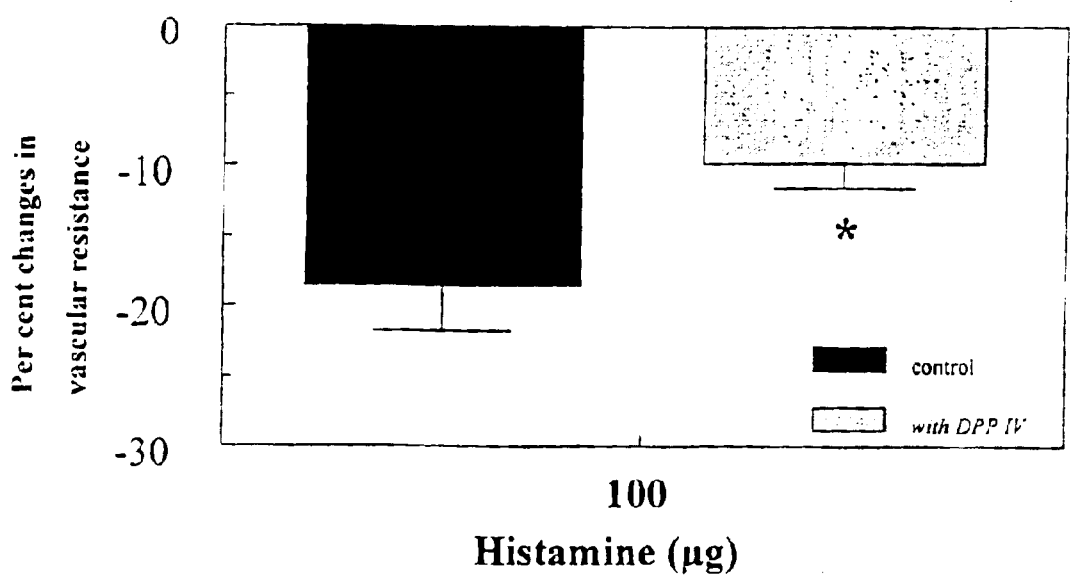
FIG. 2.
Figure 3:
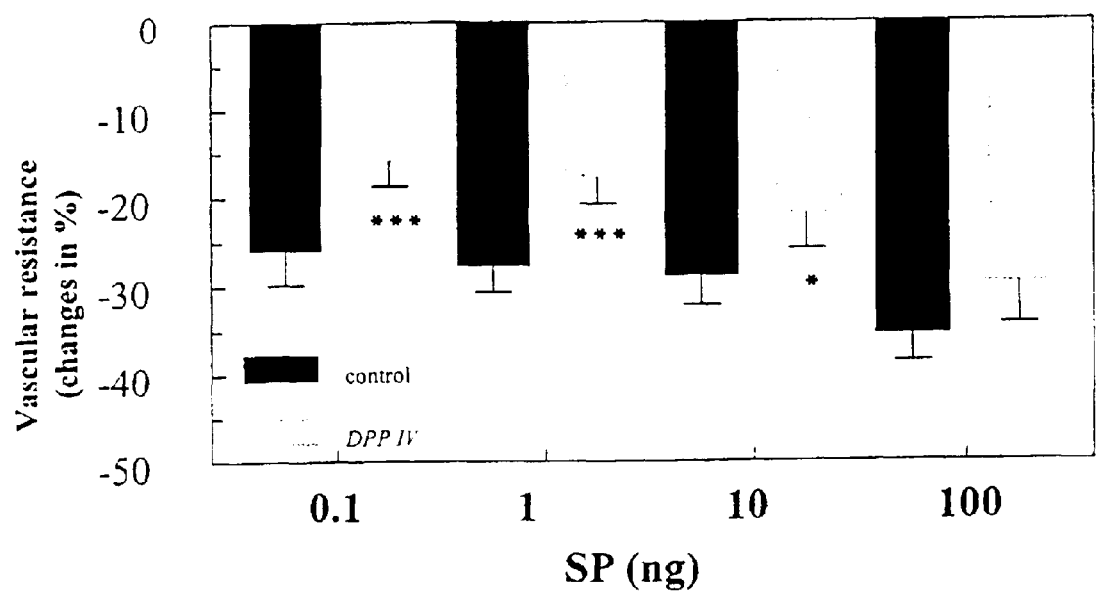
FIG. 3.

In other experiments, histamine was administered to rabbits to induce vasodilation in the femoral artery of rabbits and vascular resistance was measured. It was found that pretreatment with intravenous DPP IV led to substantially reduced histamine activity (FIG. 2). Similar results were obtained in experiments measuring vasodilation directly induced by substance P (FIG. 3). These results provide support for the view that DPP IV inhibits the action of substance P and can be administered in vivo to attenuate its activity.

All references cited are fully incorporated by reference. Having now fully described the invention, it will be understood by those of skill in the art that the invention may be performed within a wide and equivalent range of conditions, parameters and the like, without affecting the spirit or scope of the invention or any embodiment thereof.

What is claimed is:

1. A method of treating a patient for a substance P-related disease or condition, comprising administering to said patient a therapeutically effective amount of a peptidase selected from the group consisting of: SEQ ID NO: 1; SEQ ID NO:2; SEQ ID NO:3; and SEQ ID NO:4;

and wherein said disease or condition is selected from the group consisting of:
neuropathic pain; postherpetic pain; arthritic pain; and pain associated with an inflammatory condition.

2. The method of claim 1, wherein said peptidase is that of SEQ ID NO:1.

3. The method of claim 1, wherein said peptidase is that of SEQ ID NO:2.

4. The method of claim 1, wherein said peptidase is that of SEQ ID NO:3.

5. The method of claim 1, wherein said peptidase is that of SEQ ID NO:4.

6. The method of any one of claims 2–5, wherein said disease or condition is neuropathic pain.

7. The method of any one of claims 2–5, wherein said disease or condition is postherpetic pain.

8. The method of any one of claims 2–5, wherein said disease or condition is arthritic pain.

9. The method of any one of claim 8, wherein said arthritic pain is due to rheumatoid arthritis.

10. The method of any one of claim 8, wherein said arthritic pain is due to osteoarthritis.

11. The method of any one of claims 2–5, wherein said peptidase is administered at a dose of between 1 µg and 1 mg.

* * * * *